(12) United States Patent
Liang et al.

(10) Patent No.: US 8,544,331 B2
(45) Date of Patent: Oct. 1, 2013

(54) PARAMETER INDEPENDENT DETECTION OF ROTATING MACHINERY FAULTS

(75) Inventors: Ming Liang, Orleans (CA); Iman Soltani Bozchalooi, Gatineau (CA)

(73) Assignee: University of Ottawa, Ottawa, Ontario (CA)

( * ) Notice: Subject to any disclaimer, the term of this patent is extended or adjusted under 35 U.S.C. 154(b) by 798 days.

(21) Appl. No.: 12/631,528

(22) Filed: Dec. 4, 2009

(65) Prior Publication Data

US 2010/0139403 A1 Jun. 10, 2010

Related U.S. Application Data

(60) Provisional application No. 61/119,954, filed on Dec. 4, 2008.

(51) Int. Cl.
*G01M 13/00* (2006.01)
(52) U.S. Cl.
USPC .............................. 73/660; 73/659
(58) Field of Classification Search
USPC ............................ 73/660, 659, 593
See application file for complete search history.

(56) References Cited

U.S. PATENT DOCUMENTS

| | | |
|---|---|---|
| 4,493,042 A | 1/1985 | Shima et al. |
| 4,790,190 A | 12/1988 | Bambara et al. |
| 4,843,885 A | 7/1989 | Bambara et al. |
| 4,872,337 A | 10/1989 | Watts et al. |
| 5,115,671 A | 5/1992 | Hicho |
| 5,150,618 A | 9/1992 | Bambara |
| 5,381,692 A | 1/1995 | Winslow et al. |
| 5,446,451 A | 8/1995 | Grosskopf |
| 5,524,631 A | 6/1996 | Zahorian et al. |
| 6,053,047 A | 4/2000 | Dister et al. |
| 6,321,602 B1 | 11/2001 | Ben-Romdhane |
| 6,681,634 B2 | 1/2004 | Sabini et al. |
| 6,802,221 B2 | 10/2004 | Hedeen et al. |
| 6,901,353 B1 | 5/2005 | Huang et al. |
| 6,905,470 B2 | 6/2005 | Lee et al. |
| 7,136,434 B2 | 11/2006 | Hwang et al. |
| 7,222,074 B2 | 5/2007 | Zhou |
| 7,282,028 B2 | 10/2007 | Kim et al. |
| 7,283,962 B2 | 10/2007 | Meyerhoff et al. |
| 8,073,634 B2 * | 12/2011 | Liang et al. ..................... 702/22 |
| 2007/0078611 A1 * | 4/2007 | Huang et al. ................... 702/56 |

OTHER PUBLICATIONS

R.T. Rato, M.D. Ortigueira, A.G. Batista, "On the HHT, its problems, and some solutions"; ScienceDirect: Mechanical Systems and Signal Processing 22 (Jan. 2008) pp. 1374-1394.*
J. R. Stack, R. G. Harley and Thomas. G. Habetler, "An Amplitude Modulation Detector for Fault Diagnosis in Rolling Element Bearings," *IEEE Transactions on Industrial Electronics*, vol. 51, No. 5, 2004, pp. 1097-1102.

(Continued)

*Primary Examiner* — Peter Macchiarolo
*Assistant Examiner* — Rose M Miller
(74) *Attorney, Agent, or Firm* — DiBerardino McGovern IP Group LLC

(57) ABSTRACT

A parameter-free method to analyze sensor signals incorporates two or more of frequency demodulation, amplitude demodulation and phase demodulation of the raw signal data. The resulting signal is transformed to a frequency domain, and target fault characteristics from the demodulated signal are identified. The method is used to detect faults in bearings, gears and other mechanical components.

14 Claims, 14 Drawing Sheets

(56) References Cited

OTHER PUBLICATIONS

Y. Zhan and C. K. Mechefske, "Robust Detection of Gearbox Deterioration Using Compromised Autoregressive Modeling and Kolmogorov-Smirnov Test Statistics—Part I: Compromised Autoregressive Modeling with the Aid of Hypothesis Tests and Simulation Analysis," *Mechanical Systems and Signal Processing 21*, 2007, pp. 1953-1982.
P. D. McFadden, "Determining the Location of a Fatigue Crack in a Gear from the Phase of the Change in the Meshing Vibration," *Mechanical Systems and Signal Processing 2*, 1988, pp. 403-409.
P. D. McFadden, "Examination of a Technique for the Early Detection of Failure in Gears by Signal Processing of the Time Domain Average of the Meshing Vibration", *Mechanical Systems and Signal Processing*, 1 (2), 1987, pp. 173-183.
M.E. Badaoui, F. Guillet and J. Daniere, "New Applications of the Real Cepstrum to Gear Signals, Including Definition of a Robust Fault Indicator," *Mechanical Systems and Signal Processing 18*, 2004, pp. 1031-1046.
W. J. Wang and P. D. McFadden, "Application of Orthogonal Wavelets to Early Gear Damage Detection," *Mechanical Systems and Signal Processing*, 9 (5), 1995, pp. 497-507.
Z. Feng and F. Chu, "Application of Atomic Decomposition to Gear Damage Detection," Journal of Sound and Vibration 302, 2007, pp. 138-151.
James F. Kaiser, "On a Simple Algorithm to Calculate the 'Energy' of a Signal" CH2847-2/90/0000-0381, 1990 IEEE, pp. 381-384.
Ruizhong Lin, Shanan Zhu, Helei Wu, Jianfeng Zheng, "Rolling Bearings Fault Diagnosis Based on Energy Operator Demodulation Approach," *Proceedings of the 4th World Congress on Intelligent Control and Automation*, Jun. 10-14, 2002, pp. 2723-2727, Shanghai, China.
C.T. Yiakopoulos and I.A. Antoniadis, "Wavelet Based Demodulation of Vibration Signals Generated by Defects in Rolling Element Bearings," Shock and Vibration, 9, 2002, pp. 293-306.
C. Junsheng, Y. Dejie, Y. Yu, "The Application of Energy Operator Demodulation Approach Based on EMD in Machinery Fault Diagnosis," *Mechanical Systems and Signal Processing 21*, 2007, pp. 668-677.
Y. Qin, S. Qin, and Y. Mao, "Research on Iterated Hilbert Transform and its Application in Mechanical Fault Diagnosis," *Mechanical Systems and Signal Processing*, vol. 22, No. 8, 1980, pp. 1967-1980.
P. Maragos, T. F. Quatieri, and J. F. Kaiser, "Speech Nonlinearities, Modulations, and Energy Operations," CH2977-7/91 0000-0421, 1991 IEEE, pp. 421-424.
H. Li and H. Zheng, "Bearing Fault Detection Using Envelope Spectrum Based on EMD and TKEO," *Fifth International Conference on Fuzzy Systems and Knowledge Discovery*, doi 10.1109/FSKD.2008.63, 2008, IEEE pp. 142-146.
R. Maragos, J.F. Kaiser, T.F. Quatieri, "Energy Separation in Signal Modulation with Application to Speech Analysis," IEEE Transactions on Signal Processing, vol. 41, No. 10, 1993, pp. 3024-3051.
G. Zhou, J. H. L. Hansen, and J. F. Kaiser, "Nonlinear Features for Classification and Assessment of Speech Under Stress," *IEEE Transactions on Speech and Audio Processing* vol. 9, No. 3, Mar. 2001, pp. 201-216.
P. D. McFadden and J. D. Smith, "Model for the Vibration Produced by a Single Point Defect in a Rolling Element Bearing," *Journal of Sound and Vibration*, 96(1), 1984, pp. 69-82.
P. D. McFadden and J. D. Smith, "Vibration Monitoring of Rolling Element Bearing by the High-Frequency Resonance Technique—a Review," *Tribology International 17*, 1984, pp. 3-10.
H. Qiu, J. Lee, J. Lin, and G. Yu, Wavelet Filter-Based Weak Signature Detection Method and its Application on Rolling Element Bearing Prognosis, *Journal of Sound and Vibration 289*, 2006, pp. 1066-1090.
H. Qiu J. Lee, J. Lin, and G. Yu, "Robust Performance Degradation Assessment Methods for Enhanced Rolling Element Bearing Prognostics," *Advanced Engineering Informatics 17*, 2003, pp. 127-140.
J. Lin and M. J. Zuo, "Gearbox Fault Diagnosis using Adaptive Wavelet Filter," *Mechanical Systems and Signal Processing 17*, 2003, pp. 1259-1269.
I. Soltani Bozchalooi and M. Liang, "A Smoothness Index-Guided Approach to Wavelet Parameter Selection in Signal De-Noising and Fault Detection," *Journal of Sound and Vibration 30*, 2007, pp. 246-267.
I. Soltani Bozchalooi and M. Liang, "A Joint Resonance Frequency Estimation and In-Band Noise Reduction Method for Enhancing the Detectability of Bearing Fault Signals," *Mechanical Systems and Signal Processing 22*, 2008, pp. 915-933.
A. Potamianos and P. Maragos, "A Comparison of the Energy Operator and the Hilbert Transform Approach to Signal and Speech Demodulation," *Signal Processing 37*, 1994, pp. 95-120.
P. Maragos, J. F. Kaiser and Thomas F. Quatieri, "On Amplitude and Frequency Demodulation Using Energy Operators," *IEEE Transactions on Signal Processing*, 41(4), 1993, pp. 1532-1550.
A. C. Bovik, P. Maragos and Thomas F. Quatieri, "Measuring Amplitude and Frequency Modulations in Noise Using Multiband Energy Operators," *Proceedings of the IEEE-SP International Symposium on Time-Frequency and Time-Scale Analysis*, 1992, pp. 3-6.
H. M. Hanson, P. Maragos, A. Potamianos, "Finding speech formants and modulations via energy seperation: with application to Vocoder," IEEE International Conference on Acoustics, Speech, and Signal Processing, 1993, pp. 716-719.
A. C. Bovik, P. Maragos and Thomas F. Quatieri, "AM-FM Energy Detection and Separation in Noise Using Multiband Energy Operators," *IEEE Transactions on Signal Processing*, vol. 41, No. 12, 1993, pp. 3245-3265.
G. Evangelopoulos and P. Maragos, "Multiband Modulation Energy Tracking for Noisy Speech Detection," *IEEE Transactions on Audio*, vol. 14, No. 6, Speech and Language Processing, 2006, pp. 2024-2038.
B. Boashash, "Estimating and Interpreting the Instantaneous Frequency of a Signal—Part 1: Fundamentals," *Proceedings of the IEEE*, vol. 80, No. 4, 1992, pp. 520-538.
D. L. Donoho, "De-Noising by Soft-Thresholding," *IEEE Transactions on Information Theory*, vol. 41, No. 3, 1995, pp. 613-627.
H. Hong and Ming Liang, "K-Hybrid: A Kurtosis-Based Hybrid Thresholding Method for Mechanical Signal Denoising," *Journal of vibration and acoustics*, 129(4), 2007, pp. 458-470.
W. Wang "Early Detection of Gear Tooth Cracking Using the Resonance Demodulation Technique" *Mechanical Systems and Signal Processing* (2001) 15(5), 887-903.
W.J. Staszewski et al. "Application of the Wavelet Transform to Fault Detection in a Spur Gear," Mechanical Systems and Signal Processing (1994) 8(3), 289-307.
G. Dalpiaz et al. "Effectiveness and Sensitivity of Vibration Processing Techniques for Local Fault Detection in Gears" Mechanical Systems and Signal Processing (2000) 14(3), 387-412.
McFadden "Detecting Fatigue Cracks in Gears by Amplitude and Phase Demodulation of the Meshing Vibration," Journal of Vibration, Acoustics, Stress, and Reliability in Design Apr. 1986, vol. 108, 165-170.

* cited by examiner

PARAMETER INDEPENDENT DETECTION OF ROTATING MACHINERY FAULTS

CROSS REFERENCE TO RELATED APPLICATIONS

This application claims the benefit of U.S. Provisional Patent Application 61/119,954 filed on Dec. 4, 2008 which is hereby incorporated by reference in its entirety.

FIELD OF THE INVENTION

The present invention pertains to the detection of the faults of rotational machinery components including bearings, gears, shafts, cams, crankshafts and pistons via the analysis of vibration type signals acquired from machinery while in operation. The faults may have impulsive or non-impulsive characteristics.

BACKGROUND

The operation of many mechanical systems is based on the transformation of angular motions to other kinds of movement. Rotating machinery components play a crucial role in this process and are frequently used in mechanical systems. As such, effectively detecting the conditions of these components can help to reduce repair costs and maintain reliable and productive operations.

The intense loading conditions of bearings and gears together with their harsh operating environment makes them failure-prone. This is particularly true for rolling-element bearings due to their structural delicacy. Bearing failure could lead to the complete stall of a mechanical system, unplanned productivity loss for production facilities or catastrophic consequences for mission-critical equipment.

The failures of rolling-element bearings are often caused by surface faults such as cracks or spalls on bearing rollers or bearing races. Contact between the bearing faults (cracks, spalls, etc) and the mating surfaces (rollers, bearing races, etc) during the operation of the bearing generates impulses. These impulses excite a resonance in the entire system including the bearing and the structure where the bearing is mounted. The resulting high frequency resonance is typically damped out quickly due to the structural damping characteristics of the whole system. This process is repeated periodically due to the recurrence of the contact between the fault and the mating surface.

A conventional approach to detecting bearing faults involves the use of sensors such as accelerometers, vibrometers or other vibration sensors affixed to the machinery being analyzed. Preferably the sensors are placed on, or near the particular bearings under evaluation.

Raw data signals are obtained from the sensors during the operation of the machine. However, the raw data signals contain not only the fault related vibrations but also the background noise present in any measurement device, also known as intrinsic noise signals, as well as the vibrations generated by other mechanical components such as gear meshing, shaft imbalance or misalignment, also known as interference signals.

In addition, the target fault characteristic signals are typically of small amplitude compared to the interference and noise signals present in typical raw data signals. This is depicted in FIGS. 1 and 2. FIG. 1 illustrates a simulated mixture of bearing fault impulses and mechanical vibration interferences. FIG. 2 illustrates a simulated mixture of bearing fault impulses, mechanical vibration interferences and white noise arising from the operation of a normal machine with typical mechanical vibration and electrical noise.

Usually once a sufficient set of raw vibration signal data has been obtained, the raw vibration signal data is analyzed in order to discern or identify the target fault characteristic signal or signatures. In this manner, damaged or faulty machine bearings are identified.

One common approach to the analysis of the sensor raw data is known as the high frequency resonance ("HFR") approach.

FIG. 3 is a flowchart of a common HFR approach for detecting bearing faults. Raw vibration signal data is obtained from vibration sensors 20, and the band-pass filter parameters are pre-selected 21. The band-pass filter parameters include both the center frequency and the bandwidth for the band-pass filter. Once the band-pass filter parameters are selected, the vibration data signal is band-pass filtered 22. The purpose of step 22 is to ensure that all frequency components out of the range of interest, especially any low frequency large amplitude interference vibrations, have been removed from the signal. Step 22 is also necessary because amplitude demodulation of raw vibration signal data contaminated by low frequency high amplitude interference is typically ineffective for detecting bearing faults.

Amplitude demodulation is applied to the band-pass filtered signal 23, followed by spectral analysis in the form of a conventional Fast Fourier Transform of the amplitude demodulated signal 24. The Fast Fourier transformed signal is analyzed 25 to detect the target fault characteristic frequency and its harmonics. If the target fault characteristic frequency and its harmonics are detected 26, an alert signal is generated 27, otherwise the method is repeated using new raw vibration signal data until the target fault characteristic frequency and its harmonics are detected.

One major disadvantage of the HFR approach is the need to pre-select the band-pass filter parameters 21. This step presupposes significant advance knowledge of the system, including the relevant resonance frequencies and the frequency bandwidth associated with the resonance frequencies forming the frequency band of interest. If these parameters are inaccurately specified, the desired target fault characteristic signal can be reduced, distorted, or even filtered out, i.e. rejected along with the noise and interference. Therefore, optimal implementation of the HFR approach requires accurate foreknowledge of the band-pass filter parameters.

Of concern, the pre-specification of optimal band-pass filter parameters can be difficult, expensive, time consuming and sometimes impossible. These parameters can be affected by numerous variables including the bearing resonance frequencies, resonant frequencies and other vibrational characteristics of the machine and structure where the bearing is mounted. As a result, there is often uncertainty in the optimal value of the band-pass filter parameters.

Even in situations when the optimal band-pass filter parameters are known in principle, problems can still be encountered during actual machine operation, since the machine conditions can change over time. This can occur, for example, given changes in machine temperature, pressure, general machine wear, operating speed, loads, and other factors.

As a result, optimal implementation of the HFR approach requires that the band-pass filter parameters be re-selected in response to the changing machine conditions. Re-selection of the parameters is also necessary when components of the same machine are modified, or different mechanical systems are tested.

However, re-selection of the band-pass filter parameters is difficult and time consuming, since the machine conditions can change in a rapid and unpredictable manner. There is also a possibility that the machine conditions change in the process of the analysis and even before the new filter parameters have been re-selected.

Given the above factors, band-pass filters used in HFR approaches are often considered to be non-optimal and sufficiently broad so as to accommodate uncertainty in the value of the parameters or drift in the machine operating conditions. This 'detuning' ensures that the target fault characteristic signals are not rejected by the band-pass filter. However such a widening of the band-pass filter parameters also admits more noise and interference to the subsequent signal processing steps, thus undermining the usefulness of HFR approaches.

In addition to HFR approaches, there are several other known approaches for detecting bearing faults. However, many of these approaches also require pre-specification of the analysis parameters. The other approaches are briefly listed below, along with some of their fundamental disadvantages.

Attempts have been made to apply Fast-Fourier Transform ("FFT") directly to the raw vibration signal data However, the Fourier transformed signal is difficult or impossible to interpret in the presence of noise and interference. As a result, this approach is ineffective for on-line (real-time) applications where fast decisions are needed.

Bearing fault detection approaches using statistical indices to process the raw vibration signal data also exist. These approaches often suffer the disadvantages of sensitivity to irrelevant signal components. Such indices are sensitive to random, sporadic interferences and outliers, often causing false-positives or leaving faults undetected. This leads to ambiguity and poor user confidence.

The faults of mechanical components featuring impulsive and/or transient signatures, including but not limited to bearings, gears, journal bearings, slider cranks, cams, shafts, springs and dampers also need to be detected using a method which does not suffer from the deficiencies of the prior art. For example, gear faults typically include pits, chips or cracks. Contact between the fault surfaces and the mating gear tooth typically generates impulsive or transient vibrations. Similar issues arise when using the prior art signal processing techniques as summarized above to extract the fault signatures from bearings as well as other mechanical components.

In addition to the impulsive and transient fault signatures, non-impulsive signatures in the form of various signal modulations are also observed in the vibrations measured from faulty mechanical components. Such signatures are usually attributed to faults with smooth geometry such as wear. For example, gear faults featuring tooth profile distortion can lead to amplitude and phase modulations (AM and PM) of the meshing vibrations. The strength of such modulations increases with the development of faults. Hence, trend analysis on the intensity of modulation components can be effectively used to track the health state of gears.

Most of the current gear fault detection techniques focus either on the faults with smooth geometry, e.g., wear, or on those with sudden tooth profile changes, e.g., cracked or broken teeth, but not both. There is no known method that can simultaneously capture multiple forms of fault features in order to provide more reliable fault detection results. In addition, as the faults may exhibit multiple signatures spreading over a wide frequency band, there are drawbacks to adopting a narrowband strategy as taken in many of the gear fault detection techniques proposed so far, such as the HFR method. Such methods may reject an important signal component corresponding to a specific fault symptom.

Another class of fault detection method is based on a signal that is averaged synchronously with the rotation of the gear. However, this type of method is often ineffective in extracting impulsive fault signatures.

The requirements of using accurate pre-specified analysis parameters in many fault detection approaches of the prior art render them difficult to implement and insufficiently versatile to serve a wide range of applications. Furthermore, these techniques are single-fault-type oriented and are unable to detect multiple faults of different nature. In real-world situations, these disadvantages greatly limit their applicability. A parameter-free and versatile approach to the detection of fault characteristic signals for bearings, gears and other rotational mechanical components is therefore needed.

SUMMARY OF THE INVENTION

The present invention relates to a parameter-free method to analyze sensor signals for the detection of faults in bearings, gears and other mechanical components. The method does not require advance knowledge of band-pass filter parameters, faulty component resonant frequencies, machine resonant frequencies, structural damping characteristics, dominant meshing harmonic or mathematical analysis parameters.

More specifically, the method incorporates a parameter-free frequency demodulation ("FDM"), amplitude demodulation ("ADM") and phase demodulation ("PDM") of the sensor raw data signal. Then FFT is applied to identify target fault characteristics from the demodulated signal.

In one embodiment of the invention, a mathematical transformation incorporates an arbitrary combination of ADM, PDM and FDM prior to spectral analysis. Under this approach, no prior analysis parameters are needed and no prior knowledge about the machine or structural frequencies is required. The invention can be efficiently implemented by way of the mathematical transform known as the Teager Energy Operator ("TEO"). The TEO can accomplish the functions of FDM, PDM and ADM in a single operation.

DETAILED DESCRIPTION OF THE INVENTION

Unless defined otherwise, all technical and scientific terms used herein have the same meaning as commonly understood by one of ordinary skill in the art to which this invention belongs.

As used herein, the term "raw vibration signal data" refers to a signal obtained from one or more sensors, before any signal processing has been applied.

The term "de-noised vibration signal data" refers to the signal data obtained by pre-processing raw vibration signal data using an intrinsic noise removal technique.

The term "mechanical components" refers to bearings, gears, journal bearings, slider cranks, cams, shafts, springs, wheels, fans, turbines, rotors, disks, impellers, propellers, dampers and other components which are subject to faults during operation in a mechanical system.

The term "target fault characteristic signal" refers to a signal created by a fault in a mechanical component.

The term "target fault characteristic signal signature" refers to a specific feature of the target fault characteristic signal such as its frequency harmonic(s).

Figure 1:
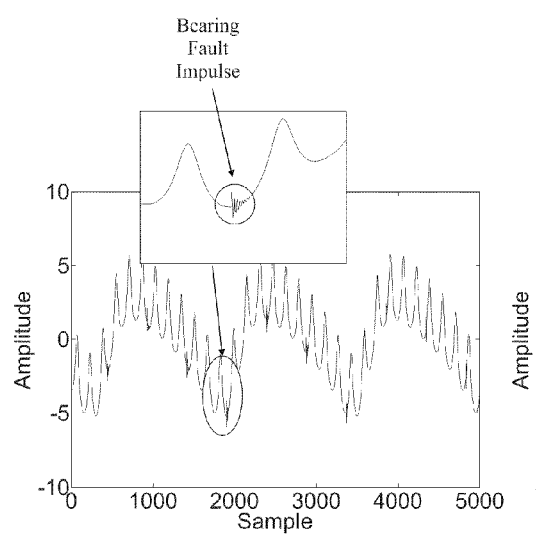
FIG. 1 illustrates a graph showing simulated sensor raw data from a machine that incorporates a faulty bearing, including bearing fault impulses mixed with mechanical vibration interferences.
Figure 2:
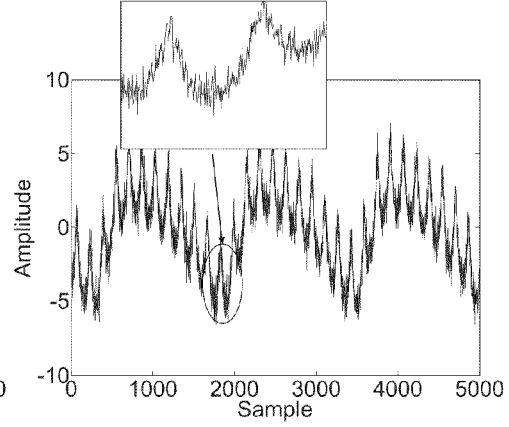
FIG. 2 illustrates a graph showing simulated sensor raw data from a machine that incorporates a faulty bearing, including: bearing fault impulses mixed with mechanical vibration interferences and white noise.
Figure 3:
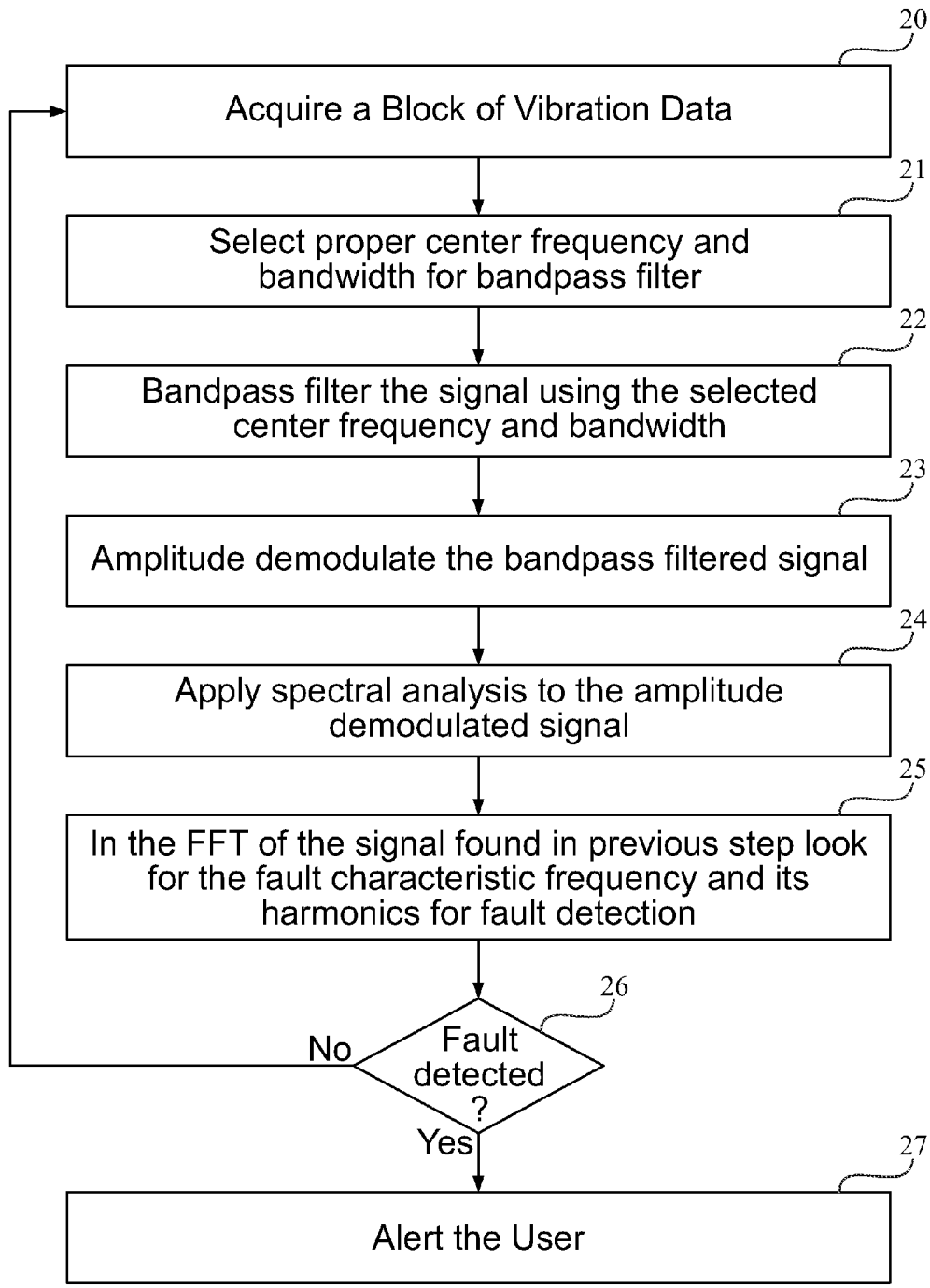
FIG. 3 is a flowchart of a typical prior art HFR approach for fault detection.
Figure 4:
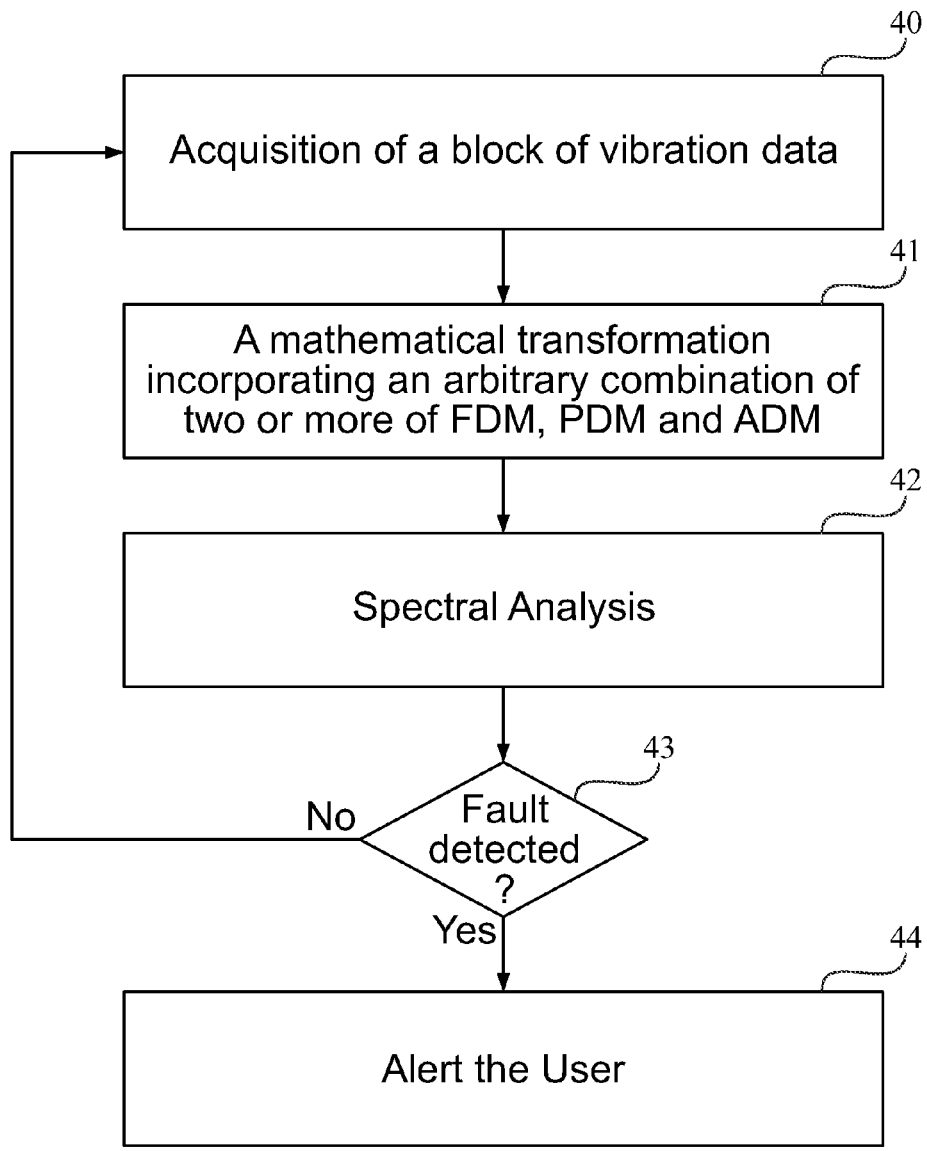
FIG. 4 is a simplified flowchart of another embodiment of the present invention for fault detection.

Referring to FIG. 4, one embodiment of the invention is shown where the raw vibration signal data is obtained 40 and transformed 41 by the application of a mathematical transformation that simultaneously incorporates an arbitrary combination of two or more of FDM, PDM and ADM prior to spectral analysis. The FDM preserves the valuable information present in the signal caused by resonance excitation associated with impulsive fault signatures. Since the frequency of the excited resonance is typically much higher than that of the interfering vibrations, the frequency demodulation also has the effect of boosting the signal to interference ratio ("SIR") which substantially facilitates the detection of weak fault induced impulsive signals. In addition, this requires none of the advance knowledge needed to enable band-pass filtering or other analysis steps required in prior art methods. The simultaneous use of the three demodulations enhances the detectability of faults with different signal characteristics, including impulsive, non-impulsive or both. Spectral analysis of the transformed signal is then performed 42. The target fault characteristic frequency and possibly several of its harmonics are detected from the spectrum of the transformed signal 43, and an alert signal is generated 44.

If a fault is not detected at step 43 the method is repeated using new raw vibration signal data until the target fault characteristic frequency and its harmonics are detected.

In another embodiment of the invention, the FDM, PDM and ADM steps are implemented in a single step by transforming the raw vibration signal data using an operator such as the TEO, which can accomplish the functions of FDM, PDM and ADM in a single operation.

The TEO applied on a discrete time signal can be expressed by the following formula:

$$\Psi_d(g(n)) = g^2(n) - g(n-1)g(n+1)$$

When applied to raw vibration signal data, the TEO has the effect of accentuating the impulsive or transient components of the signal relative to the stationary components of the signal such as gear meshing and shaft imbalance vibrations. Furthermore, TEO can extract the non-impulsive amplitude and phase modulations corresponding to faults with smooth geometry, such as wear. In addition, the TEO is computationally simple to apply and has excellent time resolution. As a result, embodiments utilizing TEO as a processing step are more responsive to fault onset in high speed rotating machinery.

Figure 5:
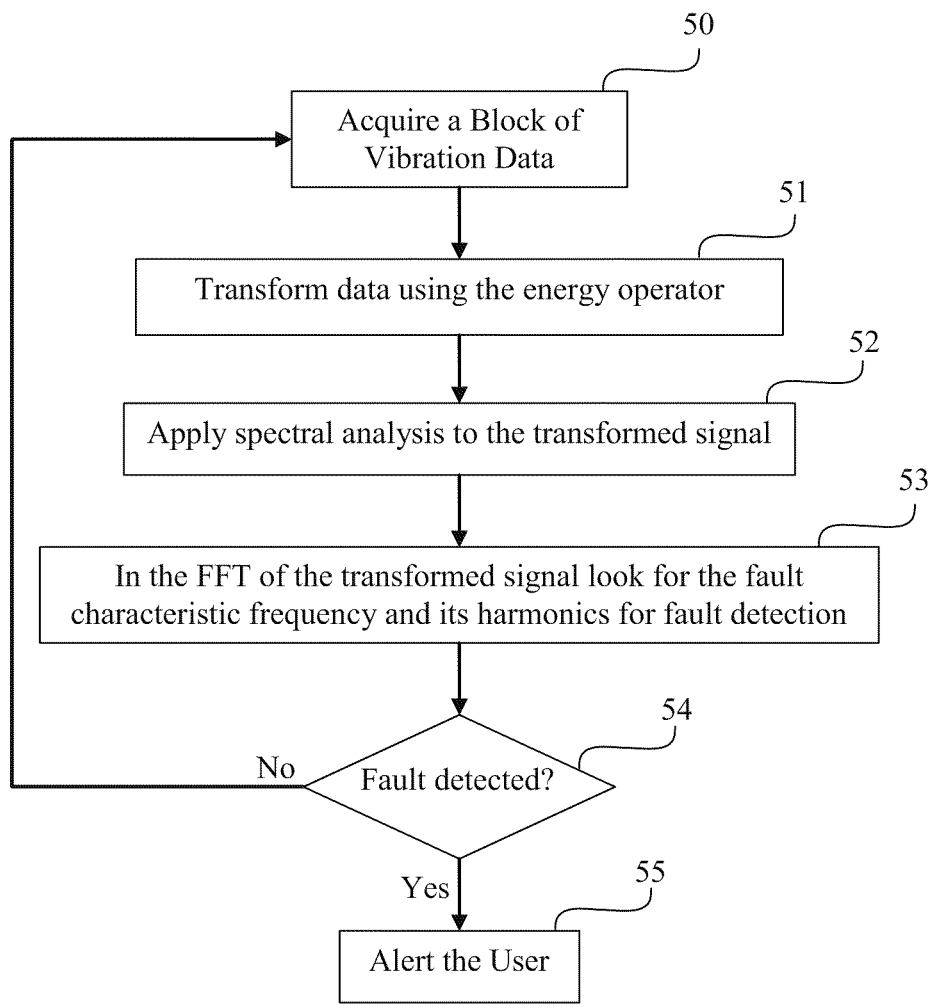
FIG. 5 is a detailed flowchart of one embodiment of the present invention.

Referring to FIG. 5, a flowchart of a fault detection method according to one embodiment of the present invention is shown. Raw vibration signal data is obtained 50 from vibration sensors during the operation of a machine. The raw vibration signal data is transformed using the TEO 51, corresponding to step 41 from FIG. 4. Spectral analysis of the transformed signal is performed 52 in the form of a conventional FFT. The Fast Fourier transformed signal is analyzed to detect the target fault characteristic frequency and its harmonics 53. If the target fault characteristic frequency and its harmonics are detected 54, an alert signal is generated 55. Otherwise, the method is repeated using new raw vibration signal data until the target fault characteristic frequency and its harmonics are detected.

Figure 6:
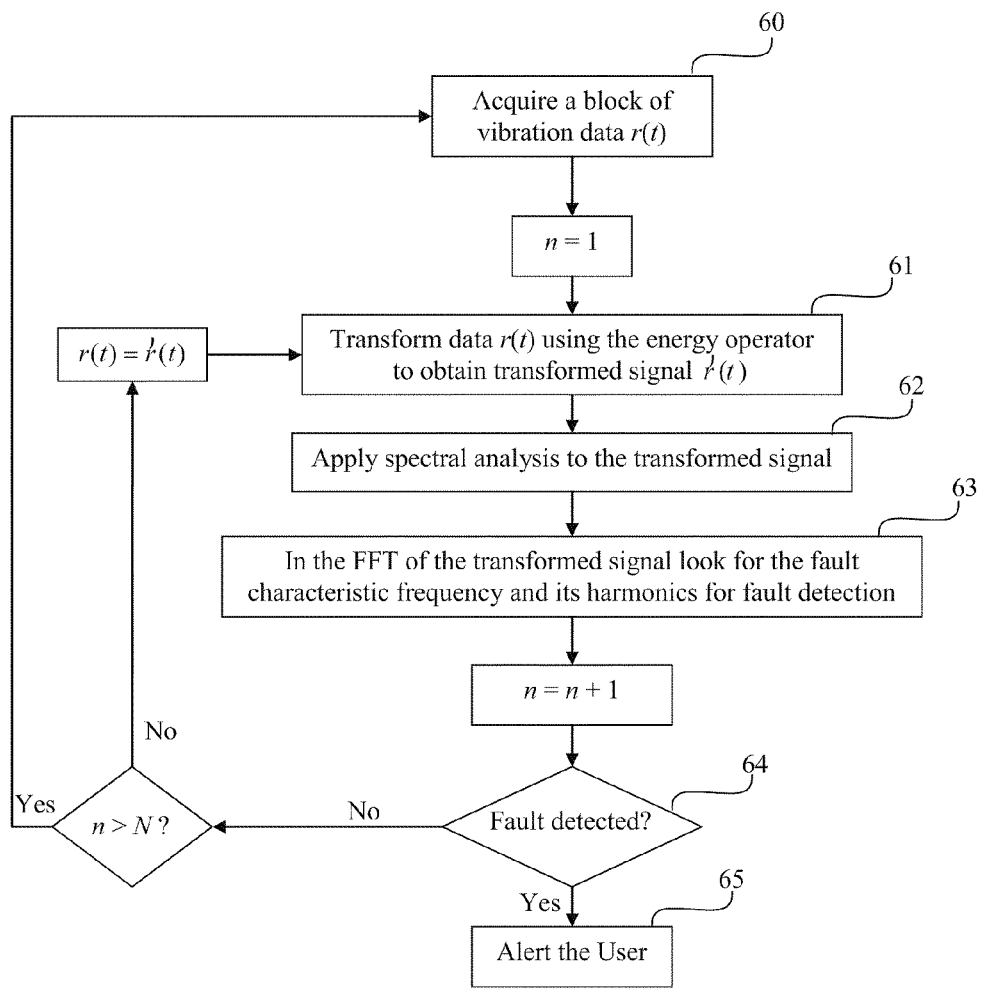
FIG. 6 is a detailed flowchart of another embodiment of the present invention.

Referring to FIG. 6, a flowchart of a fault detection method according to another embodiment of the present invention is shown. Raw vibration signal data is obtained 60 from vibration sensors during the operation of a machine. The raw vibration signal data is transformed using the TEO 61, corresponding to step 41 from FIG. 4 and similar to step 51 from FIG. 5. Spectral analysis of the transformed signal is performed 62 in the form of a conventional FFT. The Fast Fourier transformed signal is analyzed to detect the target fault characteristic frequency and its harmonics 63. If the target fault characteristic frequency and its harmonics are detected 64, an alert signal is generated 65, otherwise the transformed signal may be re-analyzed in an iterative fashion, by passing the transformed signal through repeated analysis (steps 61 to 63) until a predetermined number of iterations is reached. In this embodiment, the same raw dataset is re-analyzed to obtain a further SIR improvement which facilitates the detection of weak fault signals.

A person of ordinary skill in the art will recognize that the FFT step can be applied to the transformed signal in much the same way as in the prior art. The FFT step and other final steps of the method can accomplish spectral analysis and the identification of the same general features of the target fault characteristic signal as in the HFR approach.

Since the present invention is independent of pre-specified parameters, this results in greater ease-of-use, generality, versatility, consistency of performance and reduced cost. In addition, no prior knowledge about the bearing resonance frequencies or the structure where the bearing is mounted is required, and there are no parameters which need to be adjusted in response to changes in machine temperature, pressure, general machine wear, operating speed, loads, and other factors.

The present invention also inherently utilizes amplitude, phase and frequency modulated signal information reflected by impulsive, non-impulsive or both fault signatures. As a result, the spectrum of the energy transformed signal may contain more harmonics of the target fault characteristic signal, which contributes to more accurate fault detection results. Even in artificial situations where the prior-art optimal band-pass filter parameters are known in advance, weak bearing fault signatures are much easier to detect using the present invention due to the increased number of harmonics of the target fault characteristic signal.

The present invention also provides excellent time-resolution, which is important for pinpointing the fault onset of abruptly developed fault for on-line fault detection of mission-critical high-speed machinery.

Where the raw vibration signal data is corrupted or mixed with sufficient intrinsic background noise pre-processing of the raw vibration signal data, using intrinsic noise removal techniques may be required.

An example of a known intrinsic noise removal technique is the thresholding noise reduction or removal technique. This technique involves obtaining raw vibration signal data during quiescent conditions. The raw vibration signal data typically consists of essentially pure intrinsic noise. Specific characteristics of the intrinsic noise including but not limited to variance, are determined in order to calculate the threshold values. Once the threshold values have been calculated, denoised vibration signal data is obtained.

In addition to the frequencies of interest in this invention, namely the fault characteristic frequencies, the TEO results may also contain some cross terms such as those between a) meshing harmonics; b) sideband of one meshing harmonic and another meshing harmonic; and c) resonance and meshing harmonic. These cross terms are not useful for fault detection. The skilled worker can easily identify and preclude cross terms from being used for fault detection in accordance with the present invention as they do not coincide with fault characteristic frequencies and their associated harmonics.

Experiment I

Figure 7:
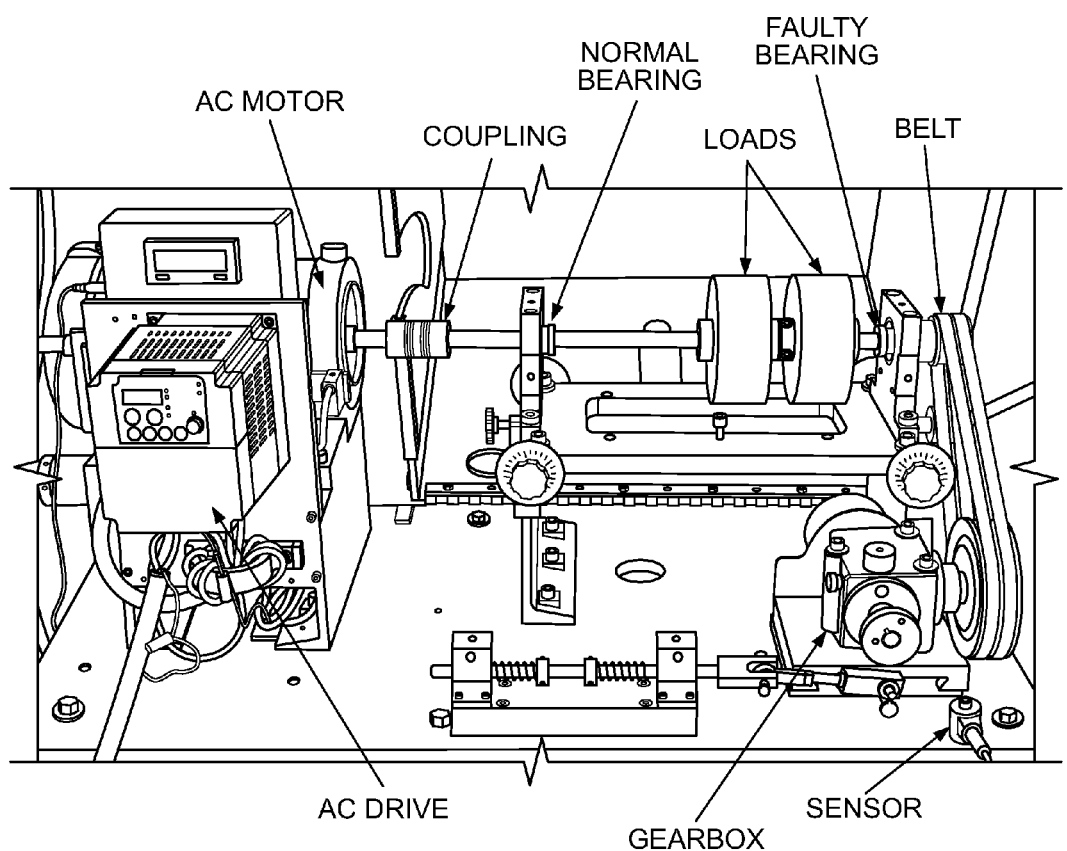
FIG. 7 illustrates the mechanical system of experiment I, which incorporates a faulty outer-race bearing.

Referring to FIG. 7, the mechanical system of experiment I, which incorporates a faulty outer-race bearing is illustrated. Experiment I was conducted using a SpectraQuest Machinery Fault Simulator (MFK-PK5M). Attached to the simulator were two well balanced mass rotors (2" thick, 4" in diameter and 11.1 lbs each) installed on a ⅝" steel shaft and supported by two type ER10K bearings (inside, outside, pitch and ball diameters are respectively 0.6250", 1.8500", 1.3190" and 0.3125") with eight rolling elements (balls). The simulator was powered by a 3-hp AC motor which was controlled by a Hitachi drive (SJ200-022NFU). The shaft speed was set at 1422 RPM (23.7 Hz). The right bearing had a pre-seeded fault created by the manufacturer on the outer race with a characteristic frequency of 72 Hz, as specified in the simulator user's manual. To create additional vibration interference, a gearbox was also connected to the driving shaft using a belt.

In experiment I, an accelerometer (Montronix VS100-100) with 100 mV/g sensitivity and 1-12 kHz sensitivity range was used to collect the raw vibration sensor data. The accelerometer was installed on the simulator base at a location not immediately proximate to the faulty bearing but proximate to the belt and the gearbox, as shown in FIG. 7. In addition to accelerometers, other acoustic or vibration sensors for measuring an acoustic emission or vibrations of a mechanical system may be used, such as a laser vibrometer, an acoustic emission sensor or a microphone The raw vibration sensor data was sampled at 20,000 samples/sec, and was subsequently analyzed by the embodiment of the invention as depicted in FIG. 5.

Figure 8:
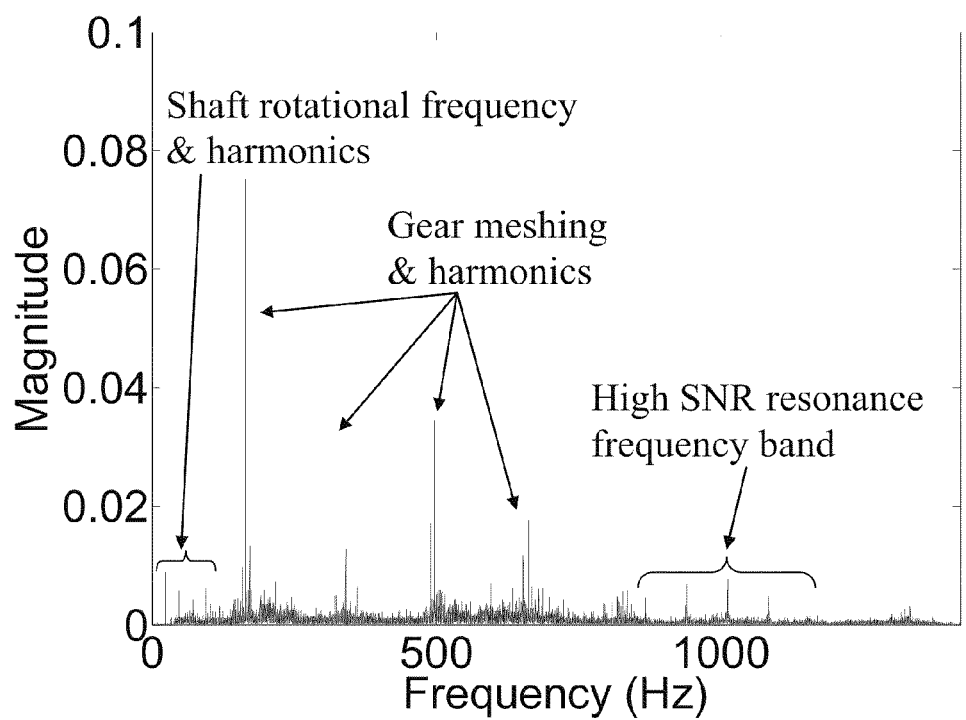
FIG. 8 illustrates the frequency domain representation of the raw vibration signal data acquired from the mechanical system of experiment I.

Referring to FIG. 8, the frequency domain representation of the raw vibration sensor data acquired from the vibration sensor from experiment I is illustrated. The frequency domain representation shows that the spectrum of the raw vibration signal data is dominated by background noise and vibration interferences which includes gear meshing and shaft imbalance. As a result, neither the fault characteristic frequency at 72 Hz, nor any of the associated harmonics can be detected from this figure.

Figure 9:
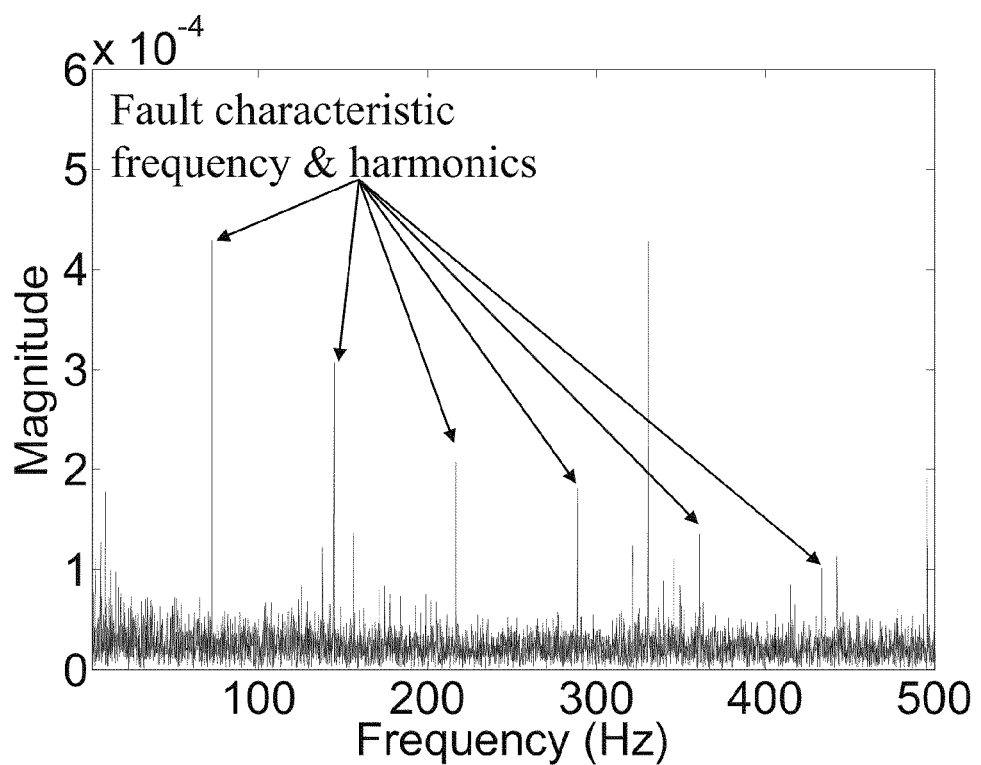
FIG. 9 illustrates the frequency domain representation of the TEO transformed signal of experiment I, obtained according to one embodiment of the invention.

Referring to FIG. 9, the frequency domain representation of the TEO transformed signal from experiment I is illustrated. The fault characteristic frequency at 72 Hz and five of the associated harmonics at 144 Hz, 216 Hz, 288 Hz, 360 Hz and 432 Hz respectively, were clearly detected. As a result, the existence of the bearing fault was confirmed when using the method of this embodiment Improvements brought about through the implementation of the invention may be appreciated by a person of ordinary skill in the art when comparing FIG. 8 with FIG. 9.

Experiment II

Figure 10:
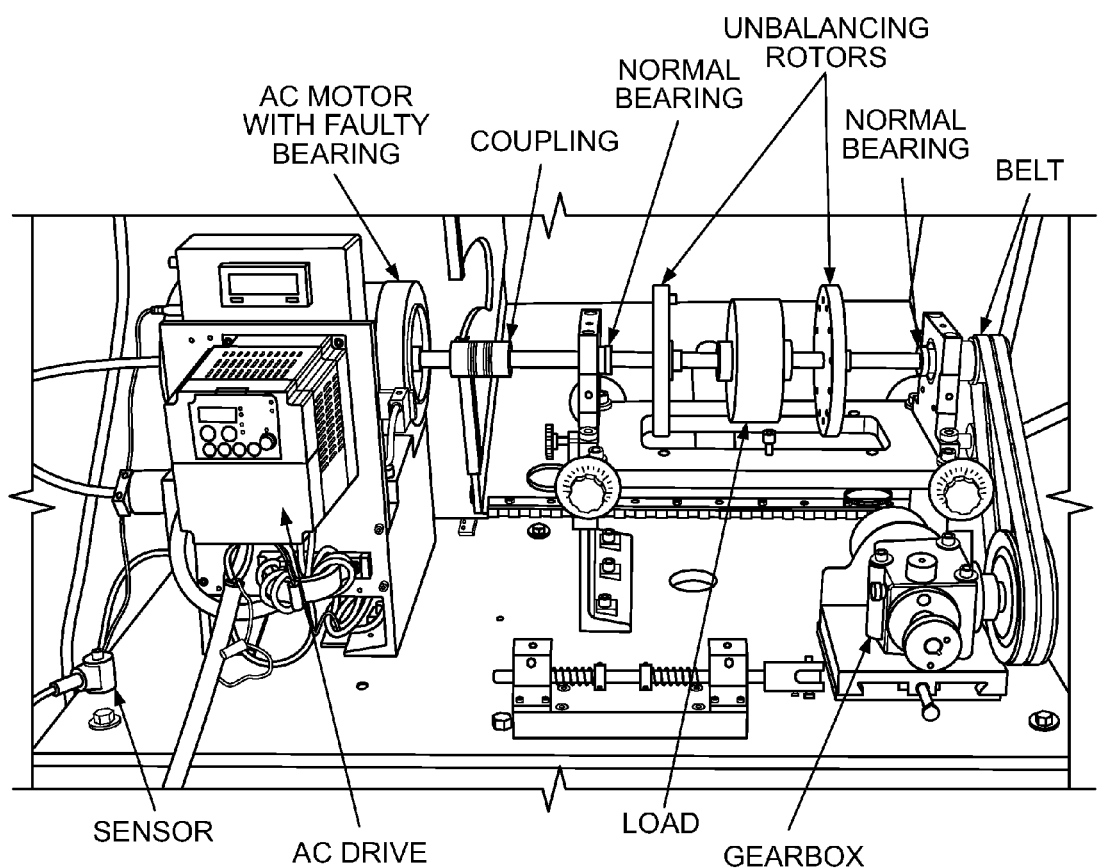
FIG. 10 illustrates the machinery of experiment II, driven by an AC motor, which incorporates a faulty inner-race bearing.

Referring to FIG. 10, the mechanical system of experiment II, driven by an AC motor incorporating a faulty inner-race bearing is illustrated. An AC motor bearing of type NSK-6203 (inside, outside, pitch and ball diameters are respectively 0.6693", 1.5748", 1.142" and 0.266") with eight rolling elements (balls) was used. A single balanced load rotor (2" thick, 4" in diameter and 11.1 lbs) was mounted on the same ⅝" steel shaft which was used in experiment I. Both bearings that supported the shaft were normal. To introduce additional vibration interferences, two unbalanced rotors were also installed on the ⅝" steel shaft, as well as a gearbox via a belt connection. The shaft speed was set at 1428 RPM (23.8 Hz). The AC motor bearing had a pre-seeded fault, which was created by the manufacturer on the inner race with a characteristic frequency of 117 Hz.

In experiment II, the raw vibration sensor data was acquired from the vibration sensor in the same fashion as in experiment I, and analyzed using the embodiment of the invention as depicted in FIG. 6.

Figure 11:
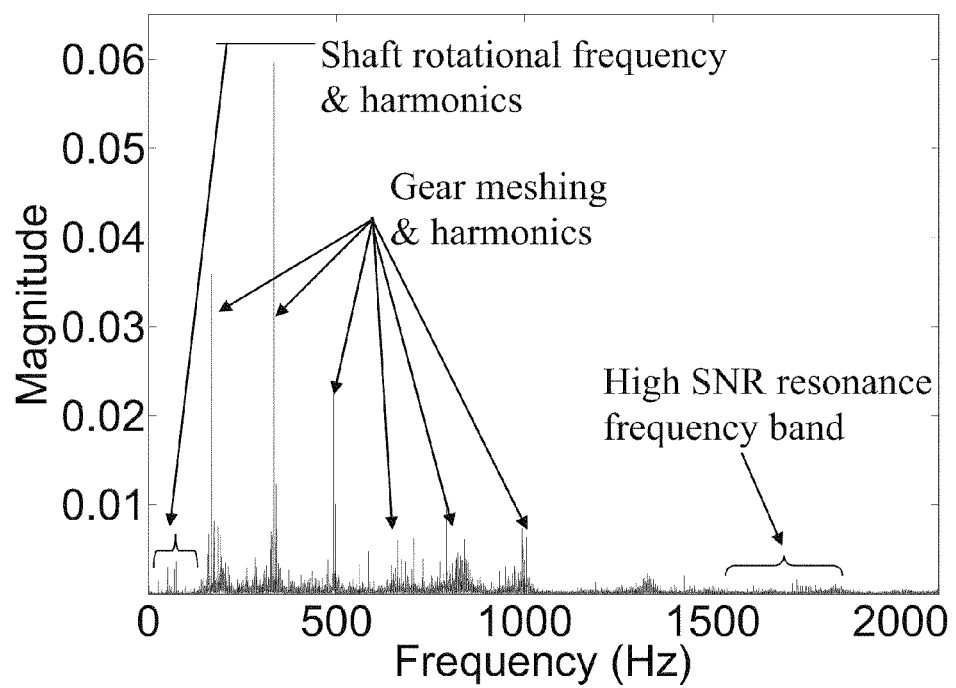
FIG. 11 illustrates the frequency domain representation of raw vibration signal data acquired from the mechanical system of experiment II.

Referring to FIG. 11, the frequency domain representation of the raw vibration signal data acquired from the mechanical system of experiment II, incorporating an AC motor with a faulty inner race bearing is illustrated. As shown in the figure, the spectrum of the raw vibration data signal is dominated by background noise and vibration interferences, and neither the fault characteristic frequency nor any of the associated harmonics can be detected from this figure. The raw vibration signal data is also transformed using TEO but in a repeated fashion according to the embodiment of FIG. 6.

Figure 12:
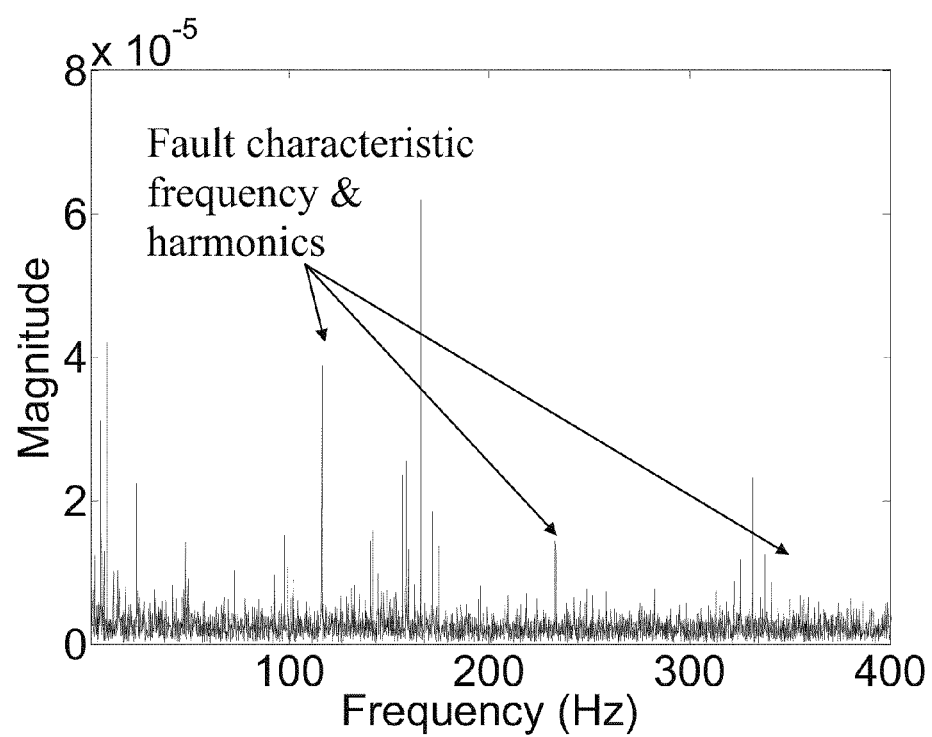
FIG. 12 illustrates the frequency domain representation of the TEO transformed signal of experiment II, obtained from one embodiment of the invention.

Referring to FIG. 12, the frequency domain representation of the transformed signal is illustrated. As shown in the figure, the fault characteristic frequency at 117 Hz and two of the associated harmonics at 234 Hz and 351 Hz respectively, were clearly detected. Consequently, the existence of the bearing fault was successfully confirmed.

Experiment III

Figures 13A, 13B:
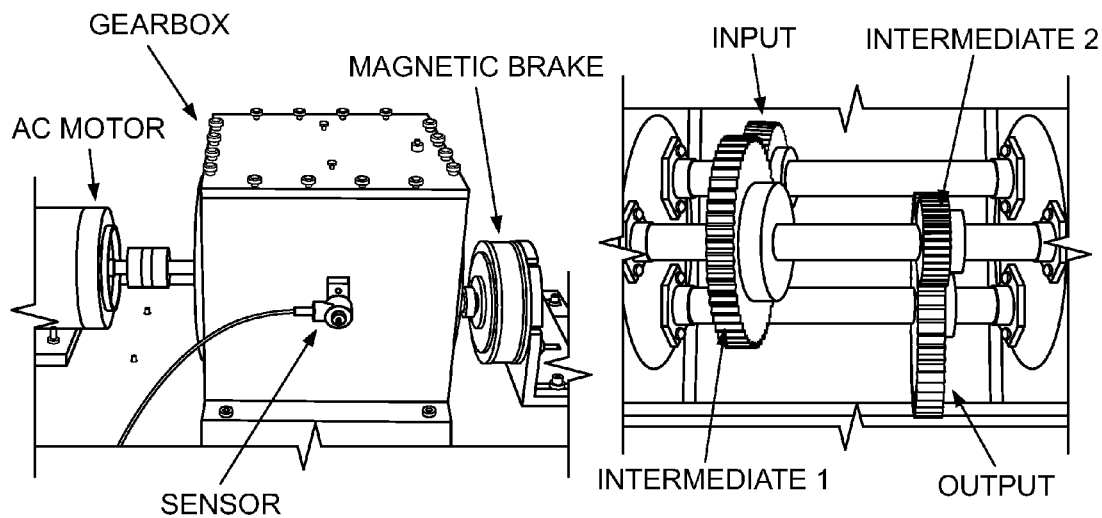
FIGS. 13 (a) and (b) illustrate the mechanical system of experiment III, a two-stage parallel gearbox which incorporates a faulty output gear.

The mechanical system of experiment III is illustrated in FIG. 13. This experiment was for a two stage parallel gearbox incorporating a faulty output gear. The faults of the output gear include dented and chipped teeth. Referring to the same figure, the input gear has 24 teeth. This gear engages with a 40 teeth intermediate gear, labeled as "Intermediate 1" in FIG. 13(b), leading to a speed reduction of 0.6. The second intermediate gear, labeled as "Intermediate 2" in FIG. 13(b), has 32 teeth and was engaged to a 96 teeth output gear. Hence, the total speed reduction was 0.2. The output shaft was connected to a Precision Tork™-Model MC6 magnetic break providing 4.7 N·m load. The same accelerometer (Montronix VS100-100) as that used in experiments I and II was placed on the casing of the gearbox, as illustrated in FIG. 13(a).

In this experiment, the shaft rotational speed was 3.54 Hz, which lead to fundamental harmonics of 3.54 Hz, 2.12 Hz, and 0.71 Hz for the input, intermediate and output gears, respectively. The output gear meshing frequency was 0.71 Hz×96 teeth=68.16 Hz.

Figure 14:
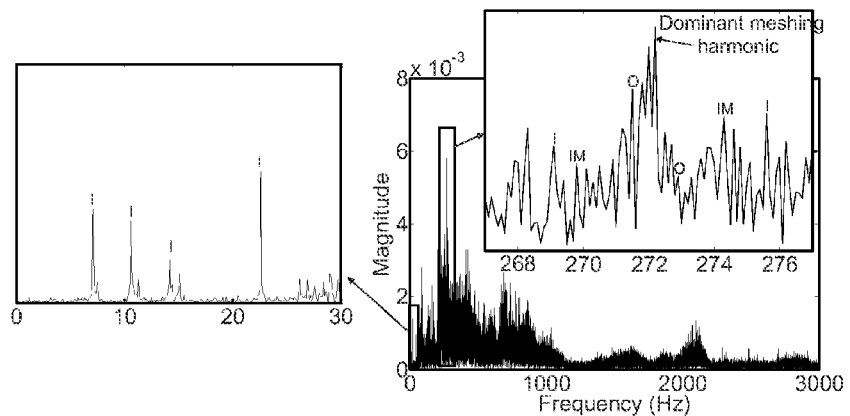
FIG. 14 illustrates the spectrum of the raw vibration signal of experiment III, including close-up views of the strongest (4th) output gear meshing harmonic at 272.64 Hz (right) and of the low frequency region covering 0-30 Hz (left)

FIG. 14 illustrates the frequency domain representation of the raw vibration signal data acquired from the mechanical system of experiment III. Two close-up views of the low frequency region, on the left, and the dominant meshing harmonic, on the right, are also included in this figure. Harmonics of the input, intermediate and output gears are denoted by "I", "IM" and "O", respectively. As shown in this figure and in its close up views, the spectrum of the raw vibration data signal was dominated by background noise and vibration interferences. Due to the manufacturing inaccuracies, a few harmonics of the rotational frequencies of output, input and intermediate gears can be observed in the spectrum of the right close-up insert but the existence of faults on the output gear cannot be concluded due to the weak signature. On the other hand, a few harmonics of the healthy input gear rotational frequency stand out on the left close-up view. This could be caused by an unbalance or the vibration of the AC motor which has the same frequency as that of the input gear shaft. However the faulty output gear signature cannot be observed from the same close-up view. The close-up view on the right shows the strongest ($4^{th}$) output gear meshing harmonic at 272.64 Hz. The close-up view on the left shows the low frequency region covering 0-30 Hz. To detect the faults, the raw vibration signal data was transformed using TEO according to the embodiment of FIG. 5.

Figure 15:
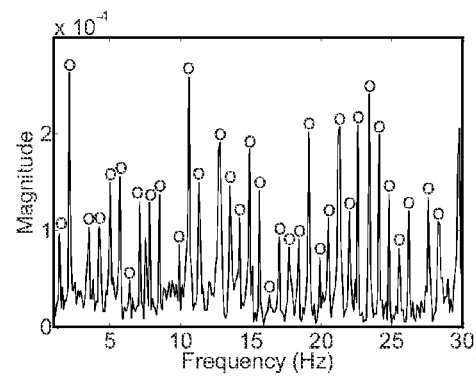
FIG. 15 illustrates the frequency domain representation of the TEO transformed signal of experiment III, obtained according to one embodiment of the invention.

Referring to FIG. 15, the frequency domain representation of the transformed signal for this experiment is illustrated. As shown in the figure, the fault characteristic frequency, i.e., rotational frequency of the output gear at 0.71 Hz and several of the associated harmonics at 1.42 Hz, 2.12 Hz, etc, (denoted by "O") were clearly observed. Consequently, the existence of the output gear faults were confirmed.

Experiment IV

Figure 16:
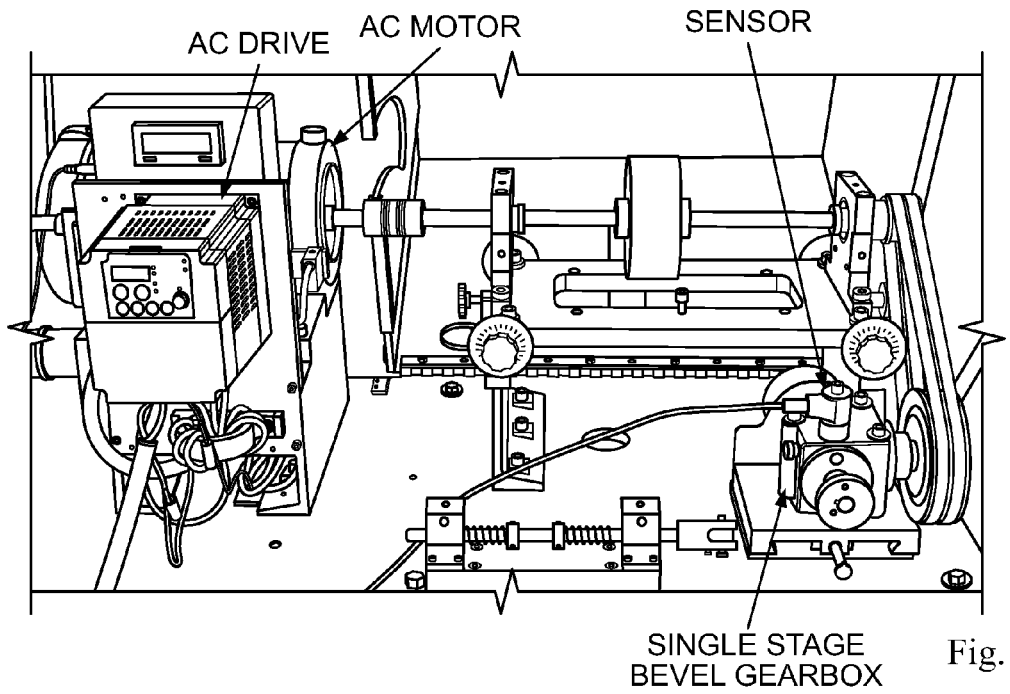
FIG. 16 illustrates the mechanical system of experiment IV, a single stage bevel gearbox which incorporates a worn gear and chipped pinion.

Referring to FIG. 16, the setup of experiment IV, consisting of a bevel gearbox with worn gear and chipped pinion is illustrated. The pinion and gear have 18 and 27 teeth, respectively. The same accelerometer (Montronix VS100-100) as that used in Experiments I, II and III was placed on the casing of the bevel gearbox to measure vibration signal. In this experiment the AC motor shaft was set to rotate at 17.3 Hz (1,040 RPM). Belt connection resulted in a speed reduction with a factor of 2.56. As such, the pinion (input gear) and output gear rotated at 6.75 Hz and 4.5 Hz, respectively. The gear meshing frequency was 6.75 Hz×18 teeth=122 Hz.

Figure 17:
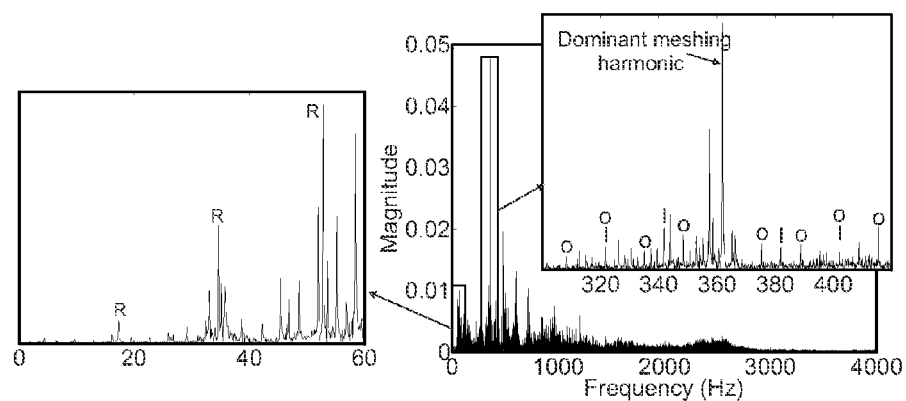
FIG. 17 illustrates the spectrum of the raw vibration signal of experiment IV, including close-up views of the strongest (3rd) meshing harmonic at 366 Hz (right) and of the low frequency region covering 0-60 Hz (left)

Referring to FIG. 17, the frequency domain representation of the raw vibration signal data acquired from the mechanical system of experiment IV is illustrated. Two close-up views of the low frequency region, on the left, and the dominant meshing harmonic, on the right, are included in this figure. Harmonics of the AC motor shaft, input (pinion) and output gears are denoted by "R", "I" and "O", respectively. Although a few harmonics of the rotational frequencies of output and input gears can be observed in the spectrum of the right close-up insert, the existence of faults cannot be firmly concluded as the signal signature is very weak. On the other hand, several harmonics of the AC motor shaft rotational frequency shown on the left close-up view are mainly due to the vibrations of the AC motor, e.g., those caused by unbalance. The close-up view on the right illustrates the strongest ($3^{rd}$) meshing harmonic at 366 Hz. The close-up view on the left shows the low frequency region covering 0-60 Hz. No peaks associated to the faulty input or output gear signatures can be observed from the same close-up view. To detect the faults, the raw vibration signal data was transformed using TEO according to the embodiment of FIG. 5.

Figure 18:
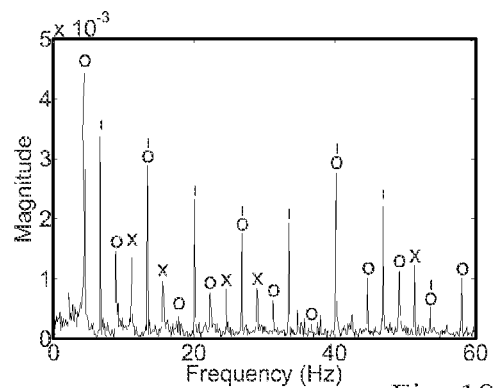
FIG. 18 illustrates the frequency domain representation of the TEO transformed signal of experiment IV, obtained according to one embodiment of the invention.
Figure 19:
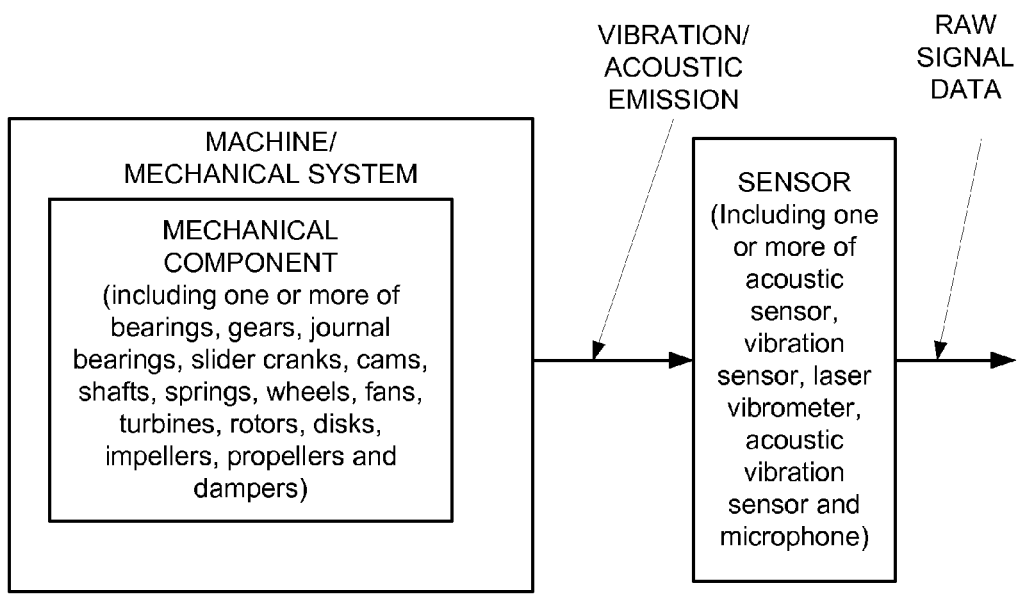
FIG. 19 illustrates a block diagram of a machine including a mechanical component and sensor configured to detect vibrations or sounds from the machine and generate raw signal data.

Referring to FIG. 18, the frequency domain representation of the TEO transformed signal is illustrated. In addition to "I" and "O" peaks, this figure also shows frequency peaks marked with "X" reflecting cross terms resulting from TEO transformation which are not useful for fault detection as they do not coincide with the fault characteristic frequencies, i.e., rotational frequencies of the input and output gears, or any harmonics of the fault characteristic frequencies. As shown in this figure, the fault characteristic frequencies, i.e., rotational frequencies of both the input and output gears respectively at 6.75 Hz and 4.5 Hz and several associated harmonics can be clearly observed. The first few associated harmonics are 13.5 Hz, 20.25 Hz, 27 Hz, and 33.75 Hz for the input (pinion) gear, and 9 Hz, 13.5 Hz, 18 Hz and 22.5 Hz for the output gear. As a result, both the output and input gear faults can be detected. However, it should be noted that the two faults are of different nature, wear for the output gear and fracture for the input pinion.

Experiments I and II demonstrate the use of ADM and FDM for detecting faults with impulsive signatures. Experiments III and IV demonstrate the application of ADM, FDM and PDM for detecting faults with both impulsive and non-impulsive characteristics. The skilled worker, having regarding to the present invention, will appreciated that other combinations of these demodulations such as ADM and PDM, as well as FDM and PDM can also be used for fault detection based on the teaching described hereinabove.

In practice, knowledge regarding the health state of a mechanical component can be of great value for scheduling maintenance and preventing disastrous breakdown consequences. The processing steps in accordance with any of the proposed embodiments can be applied continuously to vibration data acquired from an operating machine. When the existence of fault is concluded from the analysis, an alarm or alert can be activated. Proper maintenance decisions can then be made by the users or technicians in the field, so as to improve efficiency and minimize down time.

A person with ordinary skill in the art would further appreciate the effectiveness and value of the invention considering that the results illustrated in FIGS. 9, 12, 15 and 18 were obtained independent of any parameters or any prior knowledge about the mechanical system under surveillance and solely based on the available fault characteristic frequencies.

The invention claimed is:

1. A method for detecting the existence of one or more faults of one or more mechanical components of an operating machine or a mechanical system from raw signal data comprising one or more target fault characteristic signals, one or more interference signals and intrinsic noise signals, said one or more target fault characteristic signals featuring periodically occurring frequency, phase and amplitude modulations, said method comprising:

operating the machine or mechanical system including the one or more mechanical components, at least one of the one or more mechanical components being susceptible to developing one or more mechanical faults, said one or more mechanical faults each having a target fault characteristic signal, said target fault characteristic signal being created by a fault in said at least one mechanical component;

obtaining said raw signal data with one or more sensors positioned proximate to the machine;

transforming said raw signal data using one or more transformations which simultaneously incorporate any combination of two or more of frequency, phase and amplitude demodulations of said raw signal data into a new set of data;

transforming said new set of data to a frequency domain;

identifying a target fault characteristic signature from the frequency domain selected from the group consisting of an impulsive target signal, a non-impulsive target signal, a combination of multiple impulsive target signals, a combination of multiple non-impulsive target signals, and a combination of multiple impulsive and non-impulsive target signals, said target fault characteristic signature corresponding to said target fault characteristic signal;

generating an alert corresponding to the identified target fault characteristic signature detected in the machine or mechanical system.

2. The method as defined in claim 1 wherein obtaining said raw signal data includes obtaining said one or more interference signals having a frequency range which is lower than that of any resonance excited by the one or more mechanical faults.

3. The method as defined in claim 1 further comprising removing said intrinsic noise signals from said raw signal data source to transforming the raw data signal.

4. The method as defined in claim 3 wherein removing said intrinsic noise signals includes performing a thresholding noise reduction or removal technique.

5. The continuous use of the method as defined in claim 3 to monitor conditions of the machine or mechanical system comprising the one or more mechanical components.

6. The method as defined in claim 1 wherein transforming said raw signal data includes using a Teager Energy Operator.

7. The continuous use of the method as defined in claim 6 to monitor conditions of the machine or mechanical system comprising the one or more mechanical components.

8. The method as defined in claim 1 wherein obtaining said raw signal data with the one or more sensors includes obtaining said raw signal data from a sensor including one or more of source signal is obtained from an acoustic sensor configured to measure an acoustic signal of the machine or mechanical system and a vibration sensor configured to measure vibrations of the machine or mechanical system.

9. The method as defined in claim 8 wherein said vibration sensor is an accelerometer or laser vibrometer.

10. The method as defined in claim 8 wherein said acoustic sensor is an acoustic emission sensor or a microphone.

11. The method as defined in claim 1 wherein operating the machine or mechanical system including the one or more mechanical components includes operating a machine or mechanical system including a mechanical component chosen from the group consisting of one or more bearings, gears, journal bearings, slider cranks, cams, shafts, springs, wheels, fans, turbines, rotors, disks, impellers, propellers and dampers.

12. The continuous use of the method as defined in claim 1 to monitor conditions of the machine or mechanical system comprising the one or more mechanical components.

13. The method as defined in claim 1 further comprising changing operation of the machine or mechanical system.

14. The method as defined in claim 1 further comprising identifying a mechanical component corresponding to the target fault characteristic signature.

* * * * *